US006907287B1

United States Patent
Bevan et al.

(10) Patent No.: US 6,907,287 B1
(45) Date of Patent: Jun. 14, 2005

(54) DETECTING AND DISPLAYING DIAGNOSTIC INFORMATION PERTAINING TO DYNAMIC ATRIAL OVERDRIVE PACING

(75) Inventors: Gregory C. Bevan, Canyon Country, CA (US); Richard Lu, Thousand Oaks, CA (US); Harold C. Schloss, Los Angeles, CA (US); Joseph J. Florio, La Canada, CA (US); Janice Barstad, Eden Prairie, MN (US)

(73) Assignee: Packsetter, Inc., Sylmar, CA (US)

( * ) Notice: Subject to any disclaimer, the term of this patent is extended or adjusted under 35 U.S.C. 154(b) by 382 days.

(21) Appl. No.: 10/172,393

(22) Filed: Jun. 14, 2002

(51) Int. Cl.[7] ............................................. A61N 1/362
(52) U.S. Cl. ........................................................ 607/14
(58) Field of Search ...................................... 607/1–28

(56) References Cited

U.S. PATENT DOCUMENTS 5,129,392 A * 7/1992 Bardy et al. .................... 607/2
6,058,328 A   5/2000 Levine et al. ................. 607/14
6,185,459 B1  2/2001 Mehra et al. .................. 607/14

FOREIGN PATENT DOCUMENTS

WO   WO 98/32489   7/1998
WO   WO 00/09206   2/2000

* cited by examiner

Primary Examiner—Scott M. Getzow

(57) ABSTRACT

Systems and methods are provided for collecting enhanced diagnostic information specifically pertaining to overdrive pacing within an implantable cardiac stimulation device and for processing and displaying the enhanced diagnostic information using an external programmer. The enhanced diagnostic information includes one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram data, and number of rate increases. By tracking and displaying the enhanced diagnostic information, a physician can thereby more effectively and reliably program overdrive pacing control parameters to achieve optimal overdrive pacing performance.

41 Claims, 7 Drawing Sheets

DETECTING AND DISPLAYING DIAGNOSTIC INFORMATION PERTAINING TO DYNAMIC ATRIAL OVERDRIVE PACING

FIELD OF THE INVENTION

The invention generally relates to implantable cardiac stimulation devices and to external programmer devices used in connection therewith and in particular to methods and apparatus for collecting, processing and displaying diagnostic information.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, an atrial tachycardia is typically not fatal. However, atrial tachycardia reduces blood flow from the heart, increasing fatigue. Additionally, over the long term, atrial tachycardia can lead to other problems including stroke.

One technique for preventing atrial arrhythmias is dynamic atrial overdrive (DAO) pacing wherein an implantable cardiac stimulation device, such as a pacemaker or implantable cardioverter/defibrillator (ICD), applies electrical pacing pulses to the heart at a rate somewhat faster than the intrinsic atrial heart rate of the patient. In one example described in U.S. patent application Ser. No. 09/471,788, filed Dec. 23, 1999, and entitled "Methods And Apparatus For Overdrive Pacing Heart Tissue Using An Implantable Cardiac Stimulation Device", the stimulation device monitors the heart of the patient and, if two consecutive intrinsic heart beats are detected, overdrive pacing is automatically triggered. The overdrive pacing rate is based on the heart rate detected at the time overdrive pacing is triggered and is typically 5 to 10 pulses per minute (ppm) higher than the intrinsic rate. The intrinsic heart rate may be determined, for example, by calculating the time interval between the two consecutive intrinsic beats. The stimulation device then overdrive paces the heart at the selected overdrive pacing rate for a programmed number of overdrive events or "overdrive cycles". Thereafter, the stimulation device slowly decreases the overdrive pacing rate by a rate decrement specified by a programmed "recovery rate" until additional intrinsic beats are detected, then the device repeats the process to determine a new overdrive pacing rate and pace accordingly. In this manner, the heart is paced, at most times, at a rate slightly faster than the intrinsic rate and so relatively few intrinsic heart beats occur.

It is believed that overdrive pacing is effective for at least some patients for preventing or suppressing the onset of tachyarrhythmias for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods which, in turn, can trigger a tachyarrhythmia. By overdrive pacing the heart at a uniform rate, the likelihood of the occurrence of ectopic pulses is reduced and the refractory periods within the heart tissue are rendered more uniform and periodic. Thus, the dispersion of refractory periods is reduced and episodes of tachyarrhythmia are generally avoided.

Thus it is desirable within patients prone to tachyarrhythmia to ensure that most beats of the heart are paced beats, as any unpaced beats may be ectopic beats. A high percentage of paced beats can be achieved simply by establishing a high overdrive pacing rate. However, a high overdrive pacing rate has disadvantages as well. For example, a high overdrive pacing rate may be unpleasant to the patient, particularly if the artificially-induced heart rate is relatively high in comparison with the heart rate that would otherwise normally occur. A high heart rate may also cause possible damage to the heart or may possibly trigger a more serious arrhythmia, such as a ventricular fibrillation. A high overdrive rate may be especially problematic in patients suffering from heart failure, particularly if the heart failure is due to an impaired diastolic function. A high overdrive rate may actually exacerbate heart failure in these patients. Also, a high overdrive rate may be a problem in patients with coronary artery disease because increasing the heart rate decreases diastolic time and decreases perfusion, thus intensifying ischemia. Also, the need to apply overdrive pacing pulses operates to deplete a power supply of the implantable cardiac stimulation device, perhaps requiring frequent surgical replacement of the device.

Thus it is critical that the various overdrive pacing parameters (the overdrive rate, the number of overdrive cycles, the recovery rate) be set so as to achieve an optimal level of overdrive pacing sufficient to reduce the risk of a tachyarrhythmia without undue side effects. These overdrive pacing control parameters are programmed by a physician or other clinician using an external programmer device, which electronically transmits programming commands to the implanted stimulation device. Typically, the physician seeks to program the overdrive control parameters to values that will achieve a percentage of paced vs. sensed beats of 85% to 95%, i.e. 85% to 95% of the total heart beats are paced beats whereas only 5% to 15% are intrinsic beats. Unfortunately, it is quite difficult for a physician to initially determine the parameters needed to achieve a desired degree of overdrive pacing within a particular patient. Instead, the physician typically sets the various control parameters of the stimulation device of the patient to default values and then programs the device to record the resulting degree of overdrive pacing as a function of heart rate. The patient is sent home and, weeks or months later, the patient returns to the physician for a follow-up session to permit the physician to review the recorded information and to determine whether the default parameters achieved the desired degree of overdrive pacing. If the percentage of paced vs. sensed beats is too low, perhaps only 50%, the physician then either decreases the recovery rate or increases the overdrive rate or number of overdrive cycles or makes a combination of adjustments. If the percentage of paced vs. sensed beats is too high, perhaps 100%, the physician either increases the recovery rate or decreases the overdrive rate or number of overdrive cycles. The patient is again sent home and, weeks or months later, the patient again returns to the physician so that the physician can again review the recorded percentage of paced vs. sensed beats and, if needed, adjust the overdrive control parameters again. This process is usually repeated several times over a period of many months until a set of overdrive pacing control parameters are identified that come closest to achieving the desired percentage of paced vs. sensed beats.

As can be appreciated, it would be desirable to provide more effective techniques for permitting a physician to more easily determine the optimal set of control parameters so that repeated office visits are not required and so that the patient more promptly receives optimal overdrive pacing. One particular area of concerns relates to the diagnostic information provided to the physician via the external programmer that pertains to overdrive pacing. Typically, no diagnostic information specifically pertinent to overdrive pacing is detected by the implanted device and subsequently made available to the physician via the external programmer. Rather, only conventional types of diagnostic information, such as the percentage of paced vs. sensed beats, is collected. Hence, the physician must make judgments regarding the effectiveness of the overdrive pacing parameters based on limited diagnostic information. As one example, although optimal setting of the recovery rate is often critical for achieving effective overdrive pacing, conventional implantable devices typically do not provide diagnostic information directly relevant to setting the recovery rate, such as the longest recorded recovery duration or the maximum rate associated with the longest recovery duration.

Accordingly, it would be highly desirable to provide an improved implantable cardiac stimulation device capable of tracking and recording diagnostic information specifically pertinent to overdrive pacing and to provide an improved external programmer capable of processing and displaying the overdrive pacing diagnostic information. It is to these ends that the invention is primarily directed.

SUMMARY OF THE INVENTION

In accordance with the invention, a system and method are provided for collecting enhanced diagnostic information pertaining to overdrive pacing within an implantable cardiac stimulation device and for processing and displaying the enhanced diagnostic information using an external programmer. In accordance with the method, the implantable device overdrive paces the heart while tracking diagnostic information specifically pertaining to overdrive pacing, stores the overdrive pacing diagnostic information in the memory, and transmits the overdrive pacing diagnostic information to an external device for display thereon. The overdrive pacing diagnostic information tracked by the device includes one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram data, and number of rate increases.

In an exemplary embodiment, the implantable device is capable of automatic mode switching (AMS) and the overdrive pacing efficacy is represented, in one example, as a ratio of a total number of mode switching episodes to a total number of overdrive pacing episodes wherein an overdrive pacing episode is defined to occur whenever a pacing rate increase occurs during overdrive pacing that is not caused by rate recovery. In another example, overdrive pacing efficacy is represented as a ratio of a total time spent in mode switched pacing to a total time spent in overdrive pacing. The overdrive pacing percentage is represented as a percentage of time or a percentage of paced beats above the base rate or sleep rate due to overdrive pacing. The overdrive pacing histogram tracks the total number of overdrive paced beats occurring within various heart rate ranges. The intrinsic rate breakthrough histogram tracks the number of times an intrinsic breakthrough event causes an increase in overdrive rate as a function of the number of overdrive pacing cycles or as a function of the time wherein an intrinsic breakthrough event is an intrinsic beat that occurs despite overdrive pacing and usually arises when the overdrive rate has fallen below the sinus rate during rate recovery. The average associated breakthrough rate is also displayed. Actual and Modeled Overdrive Recovery plots and Overdrive vs. Intrinsic Rhythm Interaction plots are also generated. The Actual Overdrive Recovery Plot illustrates rate recovery as a function of time from the highest overdrive rate actually detected and is based on a current programmed set of overdrive pacing parameters. The Modeled Overdrive Recovery Plot illustrates rate recovery as a function of time from the same peak overdrive rate but is based on an alternate set of overdrive parameters, thereby allowing the physician to see how the alternate set of parameters would affect rate recovery. The Intrinsic Rhythm Interaction plot illustrates the overdrive rate as a function of time along with actual or predicted intrinsic rates.

By providing the physician with diagnostic information specifically pertaining to overdrive pacing, the physician can thereby more effectively and reliably program the overdrive pacing parameters of the implantable device to achieve optimal performance while reducing the number of follow-up programming sessions. Other features, advantages and objects of the invention are discussed below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Implantable Device

Figure 1:
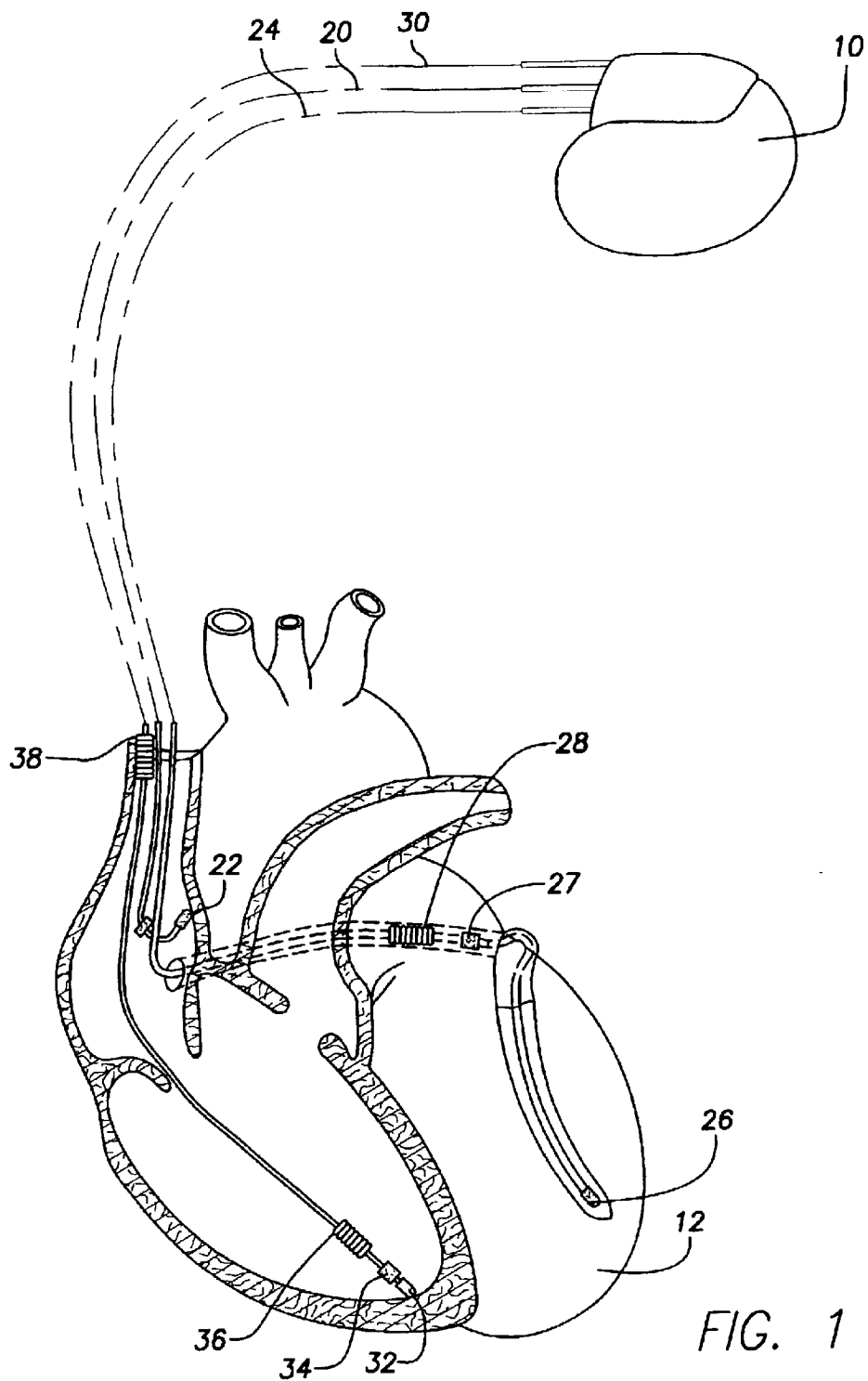
FIG. 1 is a simplified diagram illustrating an implantable stimulation device in electrical communication with at least three leads implanted into the heart of a patient for delivering multi-chamber stimulation and shock therapy and configured in accordance with the invention to perform overdrive pacing.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
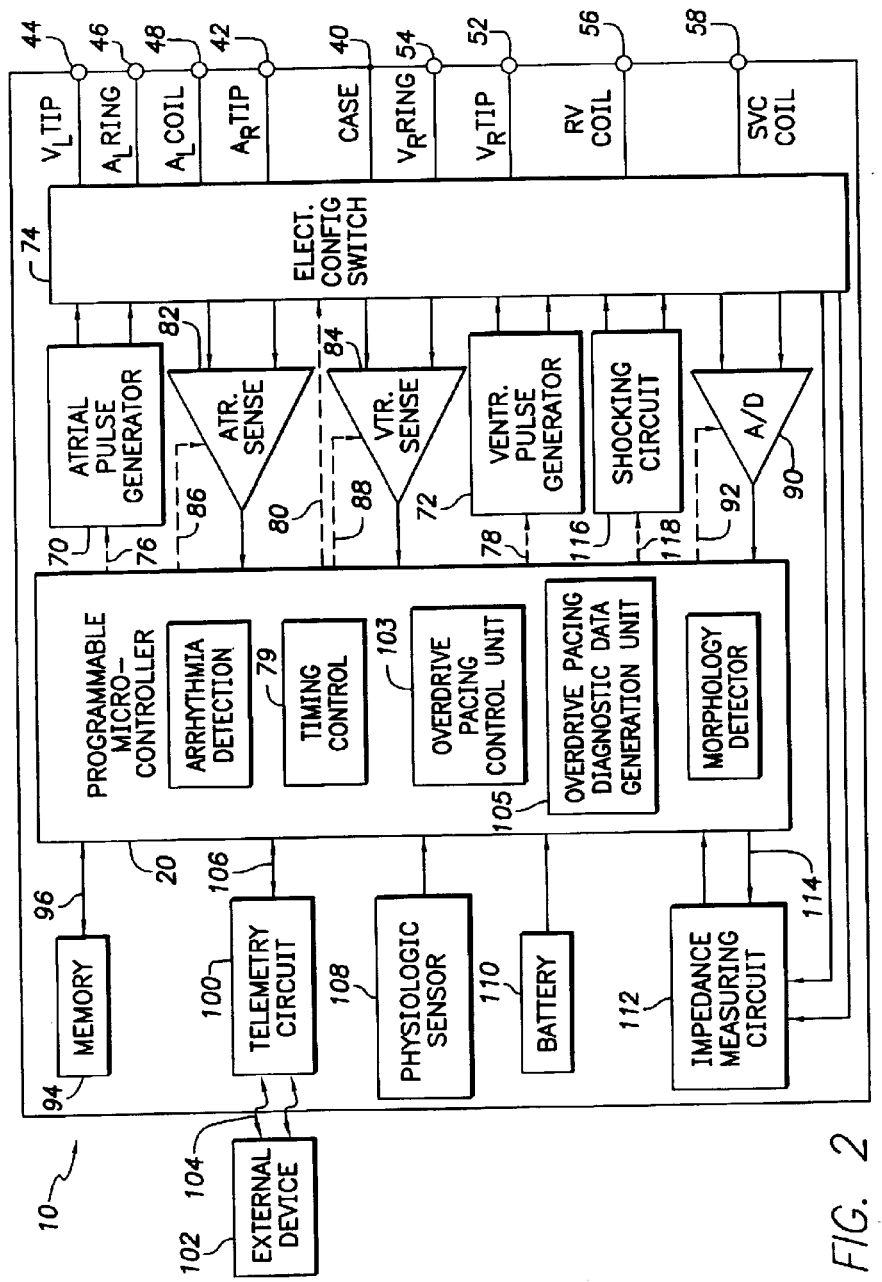
FIG. 2 is a functional block diagram of the implantable cardiac stimulation device of FIG. 1 illustrating basic elements of a stimulation device.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and 110 circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. No. 4,712,555 (Thomander et al.) and U.S. Pat. No. 4,944,298 (Sholder).

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

The microcontroller includes an overdrive pacing unit 101 for controlling overdrive pacing based on a set of additional control parameters including the overdrive pacing response function, the number of overdrive events; and the recovery rate. The overdrive pacing response function specifies the overdrive pacing rate to be applied when overdrive pacing is triggered. Overdrive pacing is triggered upon the detection of two consecutive intrinsic heart beats. The number of overdrive events specifies the number of consecutive beats to be paced following triggering of a sequence of overdrive pacing beats. The recovery rate specifies a rate decrement by which the overdrive pacing rate is to be decreased after the number of overdrive events have been paced.

In use, overdrive pacing control unit 101 monitors heart beats of the patient and, if two consecutive intrinsic heart beats are detected, overdrive pacing is triggered. The overdrive pacing rate is determined using the overdrive pacing response function and the heart rate detected at the time overdrive is triggered. The intrinsic heart rate is determined by calculating the time interval between the two consecutive intrinsic beats. Overdrive pacing unit 101 overdrive paces the heart at the selected overdrive pacing rate for a programmed number of overdrive events. Thereafter, overdrive pacing unit 101 slowly decreases the overdrive pacing rate by a rate decrement specified by the programmed recovery rate until two consecutive intrinsic beats are again detected, then the overdrive pacing unit repeats the process to determine a new overdrive pacing rate and paces accordingly. If a base rate is programmed, such as 60 bpm, the heart will be paced at the base rate even if the recovery rate would otherwise cause the rate to decrease even further. Likewise, if an alternative base rate, such as the rest rate or circadian base rate, is programmed, the pacing rate will not fall below those rates either.

While overdrive pacing is programmed, an overdrive pacing diagnostic data generation unit 103 tracks and records information specifically pertinent to overdrive pacing. The overdrive pacing diagnostic information is eventually transmitted to an external device 102, such as a programmer, transtelephonic transceiver, or a diagnostic system analyzer, via a telemetry circuit 100 for further processing and display. Specific types of overdrive pacing diagnostic information recorded by the diagnostic data generation unit and transmitted to the external device are described below.

Advantageously, the operating parameters of the implantable device 10 may be non-invasively programmed into the memory 94 through telemetry circuit 100 in telemetric communication with the external device 102. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer

Figure 3:
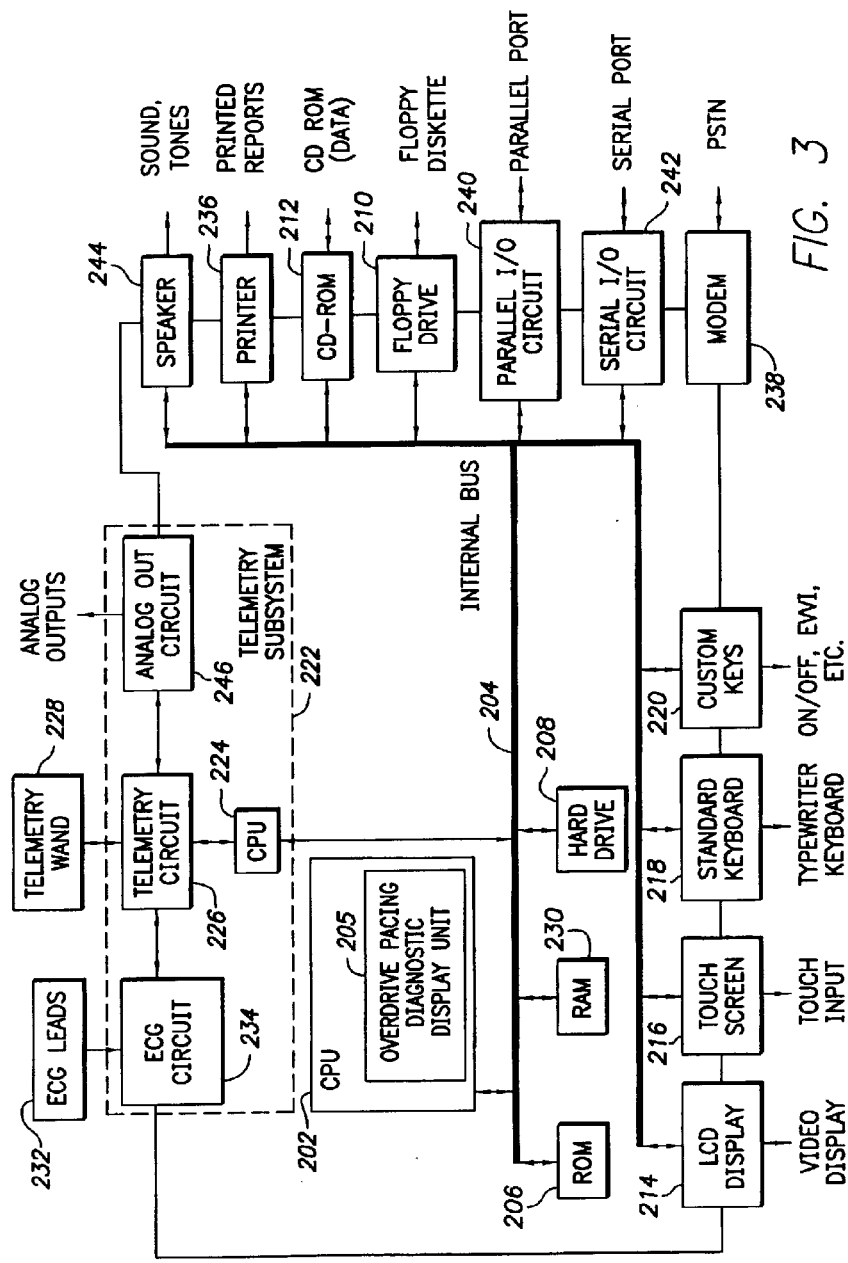
FIG. 3 is a functional block diagram illustrating components of a programmer for use in programming the implantable device of FIG. 1 and for displaying diagnostic information received from the implanted device.

FIG. 3 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EWI) key. The EVVI key sets the implanted device to a safe VVI mode with high pacing outputs. This ensures life sustaining pacing operation in nearly all situations but by no means is it desirable to leave the implantable device in the EWI mode at all times.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

As noted above, diagnostic information provided by the implantable device includes information specifically pertinent to overdrive pacing. An overdrive pacing diagnostic display unit 205 generates graphic and textual displays of the overdrive pacing diagnostic information, either alone or in combination with other diagnostic information. Specific types of overdrive pacing diagnostic information and exemplary displays are described below.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the EGG leads are stored within one or more of the storage devices of the external programmer. Typically, ECG leads output analog electrical signals representative of the EGG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time. See U.S. Pat. Nos. 4,596,255 and 4,791,936 by Snell et al., both entitled "Apparatus for Interpreting and Displaying Cardiac Events of a Heart Connected to a Cardiac Pacing Means".

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted medical device may be found in U.S. Pat. No. 5,716,382 entitled "Programmer for an Implantable Cardiac Stimulating Device". Prior to reprogramming specific parameters, the physician may control the external programmer to display any or all of the data retrieved from the implanted device or from the ECG leads, including displays of ECGs, IEGMs, and statistical patient information. Further information pertaining to the types of information which may be displayed using programmer may be found in U.S. Pat. No. 5,974,341 entitled "Method and Apparatus for Detecting and Displaying Diagnostic Information in Conjunction with Intracardiac Electrograms and Surface Electrocardiograms". Any or all of the information displayed by programmer may also be printed using a printer 236.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports might be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and are not intended to provide an exhaustive list of the functions performed by the device.

Overdrive Pacing Diagnostics

Figure 4:
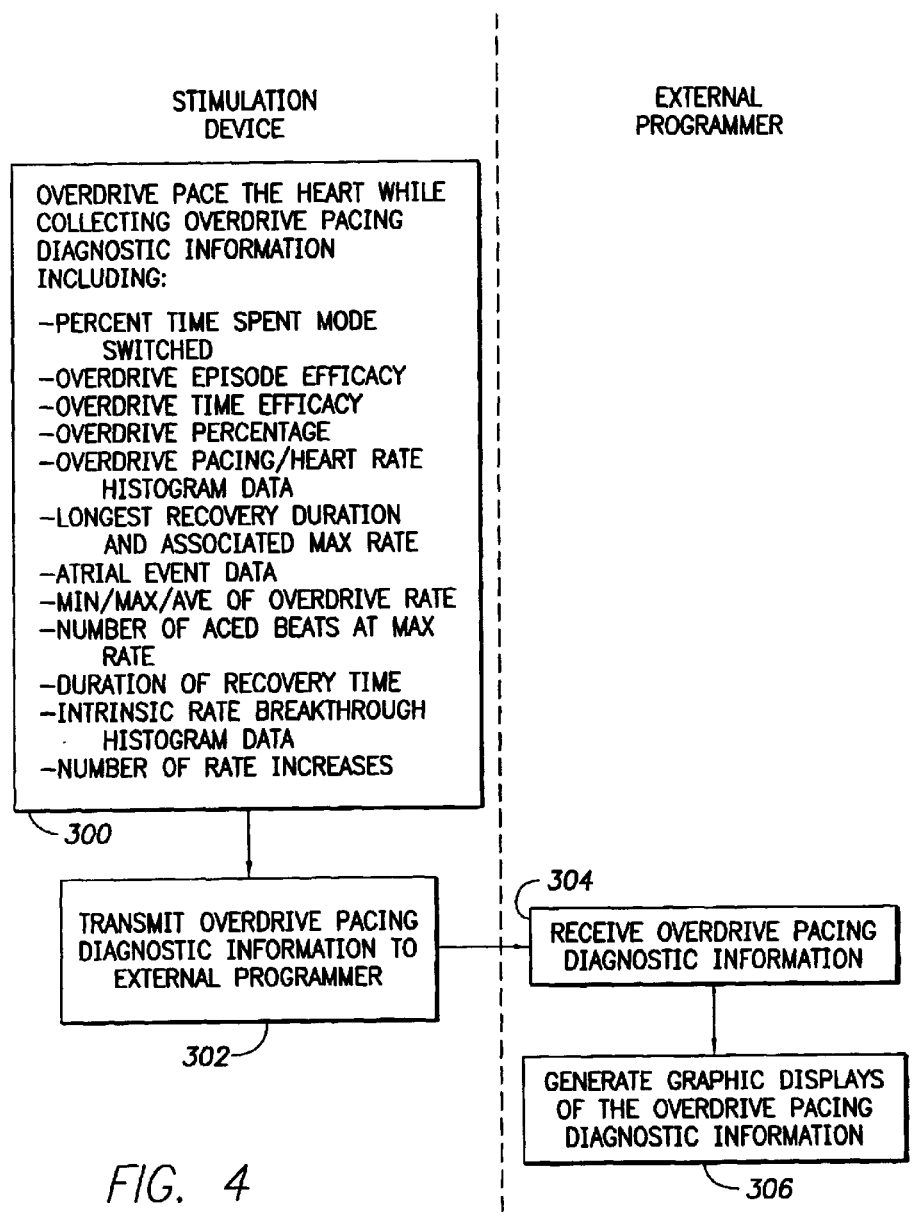
FIG. 4 is a flow chart providing an overview of steps performed by the implantable device of FIG. 2 and the external programmer of FIG. 3 to generate and display overdrive pacing diagnostic information.

Referring first to FIG. 4, a flow chart is shown describing an overview of the operation and novel features of stimulation device 10 as configured in accordance with the first embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Figure 5:
FIG. 5 is an exemplary graphic display of a variety of overdrive pacing diagnostic information provided by the external programmer of FIG. 3.

Briefly, the technique of FIG. 4 provides for the collection and display of a wide variety of diagnostic information specifically pertaining to overdrive pacing. The overdrive pacing diagnostic data generation unit of the implantable device (unit 103 of FIG. 2) collects the diagnostic information at step 300 while overdrive pacing is enabled and, upon interrogation, transfers the information to: the external programmer (FIG. 3) at step 302, which is received at step 304. The overdrive pacing diagnostic unit of the external programmer (unit 205 of FIG. 2) generates graphic displays at step 304 for review by the physician or other medical personnel. Although not specifically listed in FIG. 4, the implantable device also transmits the current set of overdrive pacing control parameters to the external programmer for display as well Exemplary diagnostic information collected by the implantable device and subsequently displayed by the external programmer includes:

Percent Time Spent Mode Switched
Overdrive Episode Efficacy
Overdrive Time Efficacy
Overdrive Percentage
Overdrive Pacing/Heart Rate Histogram
Longest Recovery Duration and Associated Max Rate
Atrial Event Data
Min/Max/Ave Of Overdrive Rate
Number Of Paced Beats At Maximum Rate
Duration Of Recovery Time from Maximum Rate
Intrinsic Rate Breakthrough Histogram Data
Number Of Rate Increases An exemplary graphic display of overdrive pacing diagnostic information and overdrive pacing control parameters is provided in FIG. 5. Additional overdrive pacing diagnostic information is shown in FIGS. 6–9.

Percent Time Spent Mode Switched

The Percent Time Spent Mode Switched provides an indication of the overall efficacy of overdrive pacing and is calculated as:

Percent Time Spent Mode Switched 100*(1−(Time in AMS)/(Total Time))

wherein a "Time in AMS" is the total time spent mode switched. This value is determined within the device by providing counters for tracking the amount of time spent mode switched and the amount of time not mode switched. The values are transmitted to the external device for calculation of the percentage therein or the device itself calculates and transmits the percentage. In either case, the external programmer displays the resulting percentage of time spent mode switched, either numerically or using any other suitable display technique, such as a pie chart. In the example of FIG. 5, a numerical display of Percent Time Spent Mode Switched of 18% is shown.

Overdrive Episode Efficacy

The Overdrive Episode Efficacy provides another indication of the efficacy of overdrive pacing and is calculated as:

Overdrive Episode Efficacy 100*(1−(AMS Episodes)/(Overdrive Episodes))

wherein an "AMS episode" is defined to occur whenever a mode switch occurs and an "overdrive episode" is defined to occur whenever a pacing rate increase occurs during overdrive pacing that is not caused by rate recovery. In other words, an overdrive pacing episode occurs whenever the overdrive rate is increased for some other reason than the detection of intrinsic breakthrough beats. Ideally, the percentage is near 100%, indicating that very few mode switch episodes have occurred. Overdrive Episode Efficacy value is determined within the device by providing counters for count the number of mode switch episodes and the number of overdrive episodes. As with the Percent Mode Switched discussed above, either the implantable device or the external programmer can calculate the Overdrive Episode Efficacy value for display by the external programmer. In FIG. 5, an exemplary numerical display of Overdrive Episode Efficacy of 82% is shown.

Overdrive Time Efficacy

The Overdrive Time Efficacy is yet another indication of the efficacy of overdrive pacing calculated as:

Overdrive Time Efficacy=100*(1−(Time in AMS) (Time in Overdrive Pacing))

wherein "time in AMS episode" and "time in overdrive pacing" are defined as above with respect to the time spent in AMS. In FIG. 5, an exemplary numerical display of Overdrive Time Efficacy of 84% is shown. Typically, the external programmer is programmed to show either Overdrive Episode Efficacy or Overdrive Time Efficacy, but not both. Both are shown in FIG. 5 for the sake of completeness.

Overdrive Percentage

The Overdrive Percentage represents either the percent of time or the percent of paced beats above the current base rate (i.e. base rate, rest rate, sleep rate) due to overdrive pacing. If based on time, the Overdrive Percentage is calculated as:

Overdrive Percentage 100*(1−(Time Above Current Base Rate)/(Total Time)).

If based on beats, the Overdrive Percentage is calculated as:

Overdrive Percentage=100*(1−(Paced Beats above Current Base Rate)/(Total

In FIG. 5, an exemplary numerical display of Overdrive Percentage of 93% is shown. Ideally, the percentage is between 85% and 95%, indicating that most beats, but not all beats, are paced. As explained above, a high percentage of paced beats may help prevent tachyarrhythmia by reducing the number of ectopic beats and thereby reducing the dispersion of refractory periods. Too high a percentage (i.e. 95–100%) may have adverse consequences on the patient. Note that the Overdrive Percentage, whether calculated as a percentage of total time or a percentage of total beats, differs from the conventional percentage of paced vs. sensed beats, which merely counts all paced beats regardless of whether the beats are paced at the base rate or at a higher overdrive pacing rate.

Overdrive Pacing/Heart Rate Histogram

The Overdrive Pacing/Heart Rate Histogram provides a record of paced beats that are caused by overdrive pacing including all base rate or rest rate paced beats, since such pacing is also overdriving the intrinsic atrial rhythm. Intrinsic beats are collected and displayed separately. By excluding non-overdrive paced beats (e.g. pacing due to rate response rather than overdrive pacing), the diagnostic thereby provides a focused profile of overdrive pacing and its interaction with the intrinsic rhythm. Preferably, the external programmer is programmed to display the actual numbers of counts detected in various heart rate ranges, as well as the percentage of counts in those ranges and also the percentage of time in those ranges. In FIG. 5, an exemplary numerical display (entitled DAO Event Counts) of exemplary histogram counts in various heart rate ranges is provided, which indicates that nearly half of all counts were sensed beats and that 38% of all beats were sensed beats above 250 ppm, possibly indicating fairly frequent episodes of tachyarrhythmia. FIG. 5 also provides an exemplary graphic display (entitled Dynamic Atrial Overdrive Histogram) of the percentage of time in the various heart rate ranges. The exemplary graphic display indicates that the heart spent only about 16% of the time above 250 ppm and that the greatest percentage of time (71%) was spent beating in the range of 70–110 ppm. The vast majority of beats in that range were paced beats. The percentage of time above 250 ppm is considerably less than the percentage of beats above 250 ppm simply because the heart is beating extremely fast in that range and hence a large number of beats occur within a relatively short amount of time.

Longest Recovery Duration and Associated Maximum Rate

The Longest Recovery Duration and Associated Maximum Rate specifies the single longest amount of time needed to reduce the pacing rate from an initial overdrive rate to a rate at which intrinsic beats are again detected. The Associated Maximum Rate specifies the highest overdrive pacing rate associated with the overdrive pacing episode having the Longest Recovery Duration. The Peak Overdrive rate is not necessarily the highest overdrive rate achieved by the device. Rather, the Peak Overdrive rate is simply the highest rate achieved during the overdrive pacing episode that had the longest recovery period. More specifically, the start of an overdrive rate recovery episode is defined as a cycle when the overdrive unit is controlling the effective pacing rate and the overdrive rate begins to drop. The end of the rate recovery episode is defined as the cycle where the overdrive rate reaches a lower limit (base rate, sensor rate, or rest rate) or when the pacing rate starts to increase for any reason. When a new overdrive rate recovery episode is longer than the previously recorded maximum duration episode, then the duration and peak rate of the new episode is stored as a new maximum value. Both the Maximum Overdrive Episode Recovery Duration and the Peak Overdrive rate are helpful for use in setting of the Number of Overdrive Pacing Cycles, which is a particularly important parameter for optimal overdrive operation.

The Longest Overdrive Episode Recovery Duration and the Associated Maximum Rate support the following diagnostic display functions:

i) The values are displayed numerically. In FIG. 5, an exemplary numerical display of Longest Overdrive Episode Recovery Duration of 12 seconds is shown. An exemplary numerical display of Associated Maximum Rate of 120 bpm is also shown.

ii) The values are used to create an Actual Overdrive Recovery plot, which begins at the recorded peak overdrive rate and shows a periodically decreasing overdrive rate based on the current programmed overdrive parameter settings. The actual overdrive recovery plot decreases until the longest recovery duration is reached, at which point an intrinsic breakthrough event triggers an increase in the overdrive rate in accordance with the current programmed overdrive parameter settings iii) The values are also used to create a Modeled Overdrive Recovery plot, which also begins at the recorded peak overdrive rate and shows a periodically decreasing rate based on an alternate set of overdrive parameters input to the external programmer by the physician.

Figure 6:
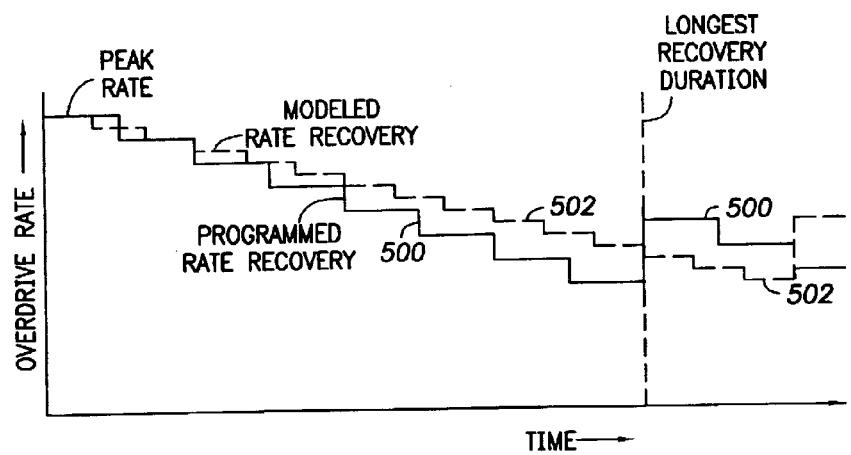
FIG. 6 is a first exemplary graphic display of an Overdrive Recovery plot displayed by the external programmer of FIG. 3.
Figure 7:
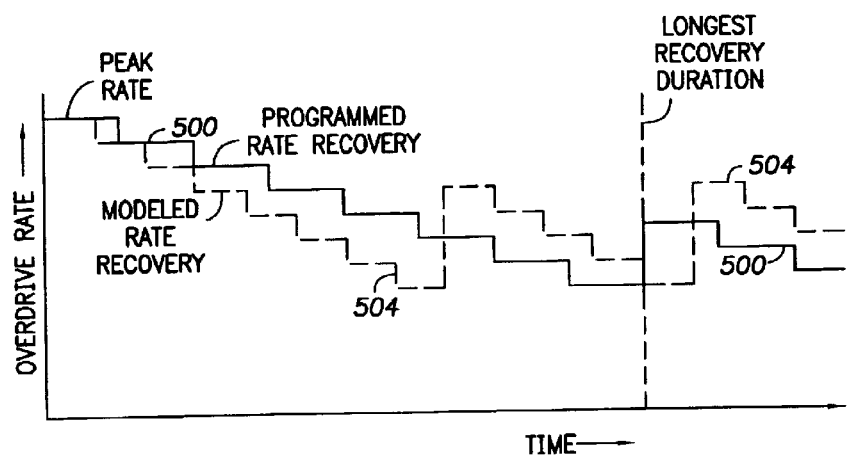
FIG. 7 is a second exemplary graphic display of an Overdrive Recovery plot displayed by the external programmer of FIG. 3.

Two examples of Actual vs. Modeled Overdrive Recovery Plots are provided in FIGS. 6 and 7. The plots are based on the same set of current overdrive pacing parameters but different sets of alternate overdrive parameters. In FIG. 6, the alternate set of overdrive parameters provides for more gradual rate recovery as compared to the current programming parameters; whereas, in FIG. 7, the alternate set provides for less gradual rate recovery. Both plots also illustrate breakthrough events triggering rate increases.

More specifically, in FIG. 6, solid line 500 represents the actual overdrive rate recovery based on the current programmed overdrive parameter settings and phantom line 502 represents the modeled overdrive rate recovery based on an alternate set of overdrive parameter settings providing more gradual rate recovery. Note that an intrinsic breakthrough event, occurring at the longest recovery duration, triggers an increase in the overdrive rate for current set of overdrive parameters (line 500). However, because the alternate set of overdrive parameters provides for more gradual rate recovery, intrinsic breakthrough does not occur for plot 502 until later. In FIG. 7, solid line 500 again represents the actual overdrive rate recovery based on the current programmed overdrive parameter settings. Phantom line 504 represents the modeled overdrive rate recovery based on an alternate set of overdrive parameters providing more aggressive rate recovery and so the intrinsic breakthrough is reached sooner.

Using these plots, the physician can easily visualize and compare the rate recovery achieved by the current set of parameters with rate recovery expected to be achieved using the alternate sets of overdrive parameters to thereby facilitate proper programming of the overdrive rate recovery parameters. Rather than providing separate displays based on separate sets of alternate programming parameters, a single display can be generated that provides the actual rate recovery plot and multiple modeled rate recovery plots for different sets of alternate parameters.

Atrial Event Data

Figure 8:
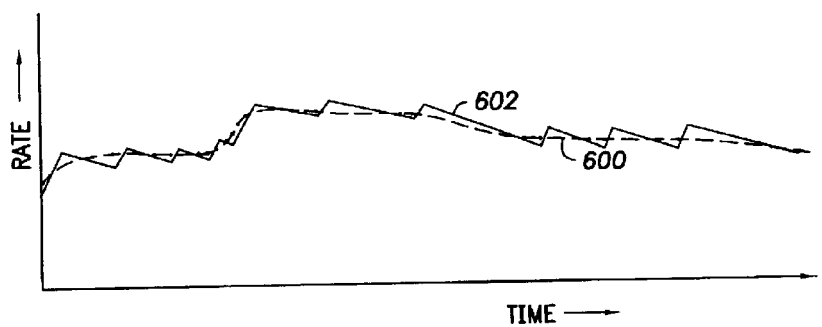
FIG. 8 is an exemplary graphic display of an Overdrive vs. Intrinsic Rhythm Interaction plot displayed by the external programmer of FIG. 3.

The Atrial Event Data provides data specifically pertaining to sensed atrial events, including the time of detection of each event. The intrinsic atrial rate is derived from the Atrial Event Data and an Overdrive vs. Intrinsic Rhythm Interaction plot is generated (FIG. 8) showing the intrinsic rate 600 as a function of time along with the overdrive rate 602. Note that the only atrial events actually sensed are breakthrough events, which occur at a rate higher than the current overdrive rate. The sensed atrial events are shown by dots in FIG. 8. The overall intrinsic rate shown in phantom lines in FIG. 8 is extrapolated from individual sensed atrial events. Hence, the intrinsic rate that is shown is merely approximate.

Min/Max/Ave Of Overdrive Rate

The Min/Max/Ave Of Overdrive Rate records the minimum, maximum, and average of the overdrive pacing rate as detected by the implanted device. In FIG. 5, an exemplary numerical display of an exemplary Min/Max/Ave of 62/122/88 is shown.

Number Of Paced Beats At Maximum Rate

The Number Of Paced Beats At Maximum Rate records the total number of paced beats recorded at the maximum rate for all overdrive pacing episodes at that maximum rate. In other words, if the highest pacing rate was detected as 120 ppm and ten overdrive pacing episodes occurred at that rate, the Number Of Paced Beats At Maximum Rate represents the sum total number of all paced beats at 120 ppm. In FIG. 5, an exemplary numerical display of an exemplary Number Of Paced Beats At Maximum Rate of 344 beats is shown. An exemplary Percentage of Beats at Maximum Rate of 3% is also displayed.

Duration Of Recovery Time from Maximum Rate The Duration Of Recovery Time from Maximum Rate specifies the length of time spent returning from the Maximum Rate to a lower limit (e.g. base rate). If multiple overdrive pacing episodes occur at the Maximum Rate, the Duration Of Recovery Time is either calculated as the average of the individual recovery times from each episode or is simply set to the recovery time of the most recent overdrive episode at the Maximum Rate. Note that the Duration Of Recovery Time from Maximum Rate differs from the Maximum Overdrive Episode Recovery Duration and the Associated Max Rate described above. One records the highest overdrive rate detected and its associated recovery duration (which may not be the longest recovery duration detected). The other records the longest recovery duration and its associated maximum rate (which may not be the highest rate detected). Both pieces of information are valuable to the physician in determining proper setting of the overdrive pacing parameters. In FIG. 5, an exemplary numerical display of an exemplary Duration Of Recovery Time from Maximum Rate of nine seconds is shown.

Intrinsic Rate Breakthrough Histogram

Figure 9:
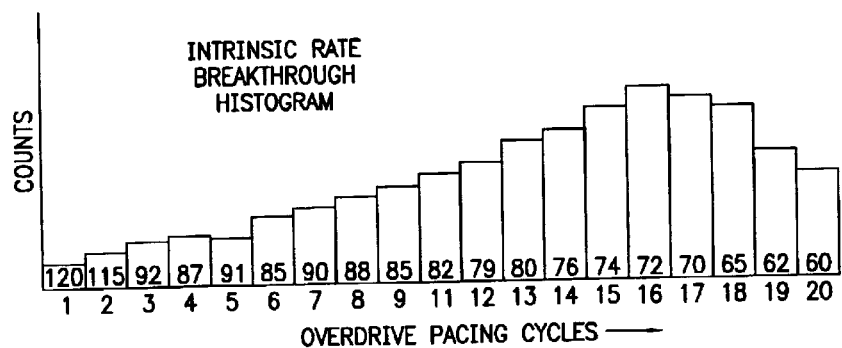
FIG. 9 is an exemplary graphic display of an Intrinsic Rate Breakthrough Histogram displayed by the external programmer of FIG. 3.

The Intrinsic Rate Breakthrough Histogram counts the number of intrinsic breakthrough events as a function of delivered overdrive pacing cycles. More specifically, the Intrinsic Rate Breakthrough Histogram consists of a set of bins, with one bin for each of the Number of Overdrive Pacing cycles. The bins are numbered from #1 to the Number of Overdrive Pacing cycles. Each time an intrinsic atrial beat causes the overdrive pacing rate to increase during delivery of overdrive pacing cycles, the bin corresponding to the current number of delivered overdrive pacing cycles is incremented. Also, whenever a bin is incremented, the pacing rate at which the breaththrough occurred is detected and the average breakthrough rate associated with that bin is updated. The associated average breakthrough rates are displayed along with the bin counts in the histogram. An exemplary Intrinsic Rate Breakthrough Histogram with associated average breakthrough rates is illustrated in FIG. 9 for an example wherein the Number of Overdrive Pacing cycles is set to twenty. Intrinsic breakthrough rates are shown for each bin. As can be seen, the greatest number of breakthrough events occurs after sixteen cycles with an average breakthrough rate of 72 bpm at that cycle. The average breakthrough rates are generally highest when the breakthrough occurs quickly. Time since initiation of the associated overdrive pacing episode is also shown along the horizontal axis.

Number of Rate Increases

The Number of Rate Increases represents the total number of times the overdrive pacing system increased the overdrive rate. This value is displayed numerically by the external programmer along with other overdrive diagnostic information. In FIG. 5, an exemplary numerical display of an exemplary Number of Rate Increases of 3425 is shown.

Overdrive Pacing Control Parameters

As noted, the external programmer also displays the current set of overdrive pacing control parameters. In FIG. 5, exemplary parameters are provided for Mode, Base Rate, Max Sensor Rate, Lower Rate Overdrive, Upper Rate Overdrive, No. of Overdrive Pacing Cycles, Rate Recovery, Automode Switch, Atrial Tachycardia Detection Rate, and AMS base rate. The Lower Rate Overdrive specifies the overdrive rate in terms of beats per minute above the current intrinsic rate for use while the intrinsic rate is below a predetermined cutoff value of, for example, 130 bpm. The Upper Rate Overdrive specifies the overdrive rate for use above the predetermined cutoff value of. Rate Recovery specifies the decrement to be applied to the overdrive rate following pacing for the No. of Overdrive Pacing Cycles. Rate Recovery includes two values: one for use with Upper Rate Overdrive, the other for use with Lower Rate Overdrive.

What have been described are various techniques detecting and displaying enhanced overdrive pacing diagnostics. Although described primarily in connection with DAO, the techniques may be exploited for either atrial or ventricular overdrive pacing. Also, although described primarily with reference to an example wherein the implanted device is an ICD, principles of the invention are applicable to other implantable cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device having a pulse generator for generating pacing pulses for applying to a heart of a patient, a control unit for controlling the pulse generator, a memory for storing information, and a telemetry unit for transmitting information to an external programmer, a method comprising:

overdrive pacing the heart while tracking diagnostic information pertaining specifically to overdrive pacing;

storing the overdrive pacing diagnostic information in the memory; and transmitting the overdrive pacing diagnostic information to an external device.

2. The method of claim 1 wherein the overdrive pacing diagnostic information comprises one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram data, and number of rate increases.

3. The method of claim 2 wherein the overdrive pacing efficacy comprises a value representative of a percentage of time not mode switched.

4. The method of claim 3 wherein the overdrive pacing efficacy comprises a value representative of a ratio of a count of mode switching episodes to a count of overdrive pacing episodes.

5. The method of claim 4 wherein an overdrive pacing episode is counted whenever an increase in an overdrive pacing rate occurs that is not caused by rate recovery.

6. The method of claim 2 wherein the overdrive pacing efficacy comprises a value representative of a ratio of an amount of time spent mode switched to an amount of time spent in overdrive pacing episodes.

7. The method of claim 6 wherein the amount of time in overdrive pacing episodes is represented as total time less any time spent mode switched less any time In sensed events less any sensor time.

8. The method of claim 2 wherein the overdrive pacing percentage comprises a value representative of a percentage of time above a base rate.

9. The method of claim 2 wherein the overdrive pacing percentage comprises a value representative of a percentage of time above a rest rate.

10. The method of claim 2 wherein the overdrive pacing percentage comprises a value representative of a percentage of paced beats above a base rate.

11. The method of claim 2 wherein the overdrive pacing percentage comprises a value representative of a percentage of paced beats above a rest rate.

12. The method of claim 2 wherein the overdrive pacing/heart rate histogram data comprises histogram values representative of the number of overdrive paced beats as a function of heart rate.

13. The method of claim 2:
wherein overdrive pacing the heart while tracking diagnostic information is performed by controlling the pulse generator to pace the heart at an initial overdrive rate for a programmed number of overdrive pacing cycles then periodically decreasing the overdrive rate by a programmed rate decrement while counting the number of consecutive rate decrements until an event triggering an increase in the overdrive rate is detected;
wherein the recovery duration for a particular overdrive pacing episode is a value representative of the number of consecutive rate decrements associated with that episode; and
wherein the longest recovery duration is a value representative of the highest number of consecutive rate decrements for all overdrive pacing episodes.

14. The method of claim 13 wherein the diagnostic data additionally comprises the maximum overdrive rate associated with the overdrive pacing episode having the longest recovery duration.

15. The method of claim 14 wherein the overdrive diagnostic data additionally comprises overdrive recovery records as a function of time.

16. The method of claim 14 wherein the diagnostic data additionally comprises overdrive recovery model data as a function of time.

17. The method of claim 2 wherein the atrial event data additionally comprises overdrive/intrinsic rhythm interaction data.

18. The method of claim 2 wherein the diagnostic data additionally comprises a value representative of the amount of recovery time from the maximum overdrive rate until a next intrinsic breakthrough event.

19. The method of claim 2 wherein the intrinsic rate breakthrough histogram data comprises values representative of a running total of intrinsic rate breakthrough events as a function of a number of cycles of overdrive pacing following initiation of each associated overdrive pacing episode.

20. The method of claim 19 wherein the intrinsic rate breakthrough histogram data additionally comprises values representative of an associated average breakthrough rate as a function of the number of cycles of overdrive pacing following initiation of each new overdrive pacing episode.

21. The method of claim 2 wherein the intrinsic rate breakthrough histogram data comprises values representative of a running total of intrinsic rate breakthrough events as a function of time following initiation of each associated overdrive pacing episode.

22. The method of claim 1 wherein the overdrive pacing diagnostic information comprises overdrive pacing efficacy.

23. The method of claim 22 wherein the overdrive pacing efficacy comprises a value representative of a percentage of time not mode switched.

24. The method of claim 23 wherein the overdrive pacing efficacy comprises a value representative of a ratio of a count of mode switching episodes to a count of overdrive pacing episodes.

25. The method of claim 24 wherein an overdrive pacing episode is counted whenever an increase in an overdrive pacing rate occurs that is not caused by rate recovery.

26. The method of claim 22 wherein the overdrive pacing efficacy comprises a value representative of a ratio of an amount of time spent mode switched to an amount of time spent in overdrive pacing episodes.

27. The method of claim 26 wherein the amount of time in overdrive pacing episodes is represented as total time less any time spent mode switched less any time in sensed events less any sensor time.

28. The method of claim 1 wherein the overdrive pacing diagnostic information comprises an overdrive pacing percentage.

29. The method of claim 28 wherein the overdrive pacing percentage comprises a value representative of a percentage of time above a base rate.

30. The method of claim 28 wherein the overdrive pacing percentage comprises a value representative of a percentage of time above a rest rate.

31. The method of claim 29, wherein the overdrive pacing percentage comprises a value representative of a percentage of paced beats above a base rate.

32. The method of claim 28 wherein the overdrive pacing percentage comprises a value representative of a percentage of paced beats above a rest rate.

33. The method of claim 1 wherein the overdrive pacing diagnostic information comprises an overdrive pacing/heart rate histogram data comprising histogram values representative of the number of overdrive paced beats as a function of heart rate.

34. In an implantable cardiac stimulation device for use with an external programmer, a system comprising:
means for overdrive pacing a heart;
means for tracking diagnostic information pertaining specifically to overdrive pacing;
means for transmitting the overdrive pacing diagnostic information to an external device.

35. The system of claim 34 wherein the means for tracking diagnostic information tracks one or more of overdrive pacing efficacy, overdrive pacing percentage, overdrive paring/heart rate histogram data, longest recovery duration, atrial event data, minimum/maximum/average of the overdrive pacing rate, number of paced beats at maximum rate, duration of recovery time from maximum rate, Intrinsic rate breakthrough histogram data, and number of rate increases.

36. In an implantable cardiac stimulation device for use with an external programmer, a system comprising:
an overdrive pacing unit operative to overdrive pace a heart;
an overdrive pacing diagnostic unit operative to track diagnostic information pertaining specifically to overdrive pacing;
a memory unit operative to store the overdrive pacing diagnostic information; and
a telemetry unit operative to transmit the overdrive pacing diagnostic information to an external device.

37. The system of claim 36 wherein the overdrive pacing diagnostic unit tracks one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram data, and number of rate increases.

38. In an external programmer for processing and displaying information received from an implantable cardiac stimulation device, a method comprising:

receiving diagnostic information pertaining specifically to overdrive pacing from the implantable device; and graphically displaying the overdrive pacing diagnostic information.

39. The method of claim 38 wherein the overdrive pacing diagnostic information comprises one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram data, and number of rate increases.

40. In a system having an implantable cardiac stimulation device and an external programmer, a method comprising:

overdrive pacing a heart using the implantable cardiac stimulation device;

tracking diagnostic information pertaining specifically to overdrive pacing using the implantable cardiac stimulation device;

storing the overdrive pacing diagnostic information in the implantable cardiac stimulation device;

transmitting the overdrive pacing diagnostic information from the Implantable cardiac stimulation device to the external programmer; and graphically displaying the overdrive pacing diagnostic information using the external programmer.

41. The system of claim 40 wherein the overdrive pacing diagnostic information tracked by the Implantable cardiac stimulation device and displayed by the external programmer comprises one or more of overdrive pacing efficacy, overdrive pacing percentage, overdrive pacing/heart rate histogram data, longest recovery duration, atrial event data, minimum/maximum/average of the overdrive pacing rate, number of paced beats at maximum rate, duration of recovery time from maximum rate, intrinsic rate breakthrough histogram date, and number of rate increases.

* * * * *